United States Patent [19]

Martin et al.

[11] Patent Number: 5,174,883
[45] Date of Patent: Dec. 29, 1992

[54] ULTRAMICROELECTRODE ENSEMBLES

[75] Inventors: Charles R. Martin, Fort Collins, Colo.; Reginald M. Penner, Irvine, Calif.

[73] Assignee: The Dow Chemical Company, Midland, Mich.

[21] Appl. No.: 240,146

[22] Filed: Sep. 2, 1988

[51] Int. Cl.⁵ .......................................... G01N 27/403
[52] U.S. Cl. ................................ 204/400; 204/153.1; 204/412; 204/434; 264/105; 427/122; 427/369; 427/430.1
[58] Field of Search .............. 204/1 T, 1 R, 400, 416, 204/418, 419, 435, 294, 434

[56] References Cited

U.S. PATENT DOCUMENTS

| | | | |
|---|---|---|---|
| 2,183,531 | 12/1939 | Allison | 204/435 |
| 3,649,498 | 3/1972 | Pretorius et al. | |
| 3,926,764 | 12/1975 | Ruzicka et al. | 204/418 |
| 4,118,305 | 10/1978 | Oloman et al. | 204/1 R |
| 4,124,453 | 11/1978 | Fleischmann et al. | 204/1 R |
| 4,206,263 | 6/1980 | Rieger et al. | |
| 4,214,968 | 7/1980 | Battaglia et al. | 204/418 |
| 4,225,410 | 9/1980 | Pace | 204/407 |
| 4,269,689 | 5/1981 | Agladze et al. | 204/1 R |
| 4,285,796 | 8/1981 | Stoner et al. | |
| 4,343,767 | 8/1982 | Long et al. | |
| 4,431,508 | 2/1984 | Brown et al. | 204/418 |
| 4,454,007 | 6/1984 | Pace | 204/418 |
| 4,551,220 | 11/1985 | Oda et al. | |
| 4,552,013 | 11/1985 | Matson | |
| 4,798,664 | 1/1989 | Yamaguchi et al. | 204/416 |

OTHER PUBLICATIONS

Sapio et al., "Analytica Chimica Acta", 67 (1973), pp. 240–242.
Kao et al., "Electrocatalysis by Electrodeposited Spherical Pt Microparticles Dispersed in Polymeric Film Electrode", *J. Am. Chem. Soc.*, (1984), 106, pp. 473–476.
Tallman et al., *J. of Liquid Chromatograph*, 6(12), 2157–2172, (1983).
Wang et al., "Ensembles of Carbon Paste Ultramicroelectrodes", *J. Electroanal. Chem.*, 249(1988) 339–345 (Jul.).
Wehmeyer et al., *Anal. Chem.* (1955) 57, 1913–1916.
"250—Å Linewidths With PMMA Electron Resist"; by: A. N. Broers et al., pp. 392–394.
Filtration Technology; "Nuclepore Membrane Filters", 1 page.
"Replication Of 175—Å Lines and Spaces In Polymethylmethacrylate Using X-Ray Lithography"; by: D. C. Flanders, pp. 93–96.
"Ensembles Of Microelectrodes: Digital Simulation By The Two-Dimensional Expanding Grid Method"; by: H. Reller et al., pp. 247–268.
"Electrochemical Characterization Of Electrodes With Submicrometer Dimensions"; by: T. Hepel et al pp. 752–757.
"Resolution Limits Of PMMA Resist For Exposure With 50kV Electrons"; by: A. N. Broers pp.166–170.
"Charge Transfer At Partially Blocked Surfaces"; by: C. Amatorre, J. M. Saveant & D. Tessier; pp. 39–51.
"Simulation Of Edge Effects In Electroanalytical Experiments By Orthogonal Collocation-VI. Cyclic Voltammetry AT Ultramicroelectrode Ensembles"; by: J. Cassidy et al.; pp. 629–636.
Technical Article–"Preparation and Electrochemical Characterization of Ultramicroelectrode Ensembles" Reginald M. Penner and Charles R. Martin.

*Primary Examiner*—T. Tung

[57] ABSTRACT

An ultramicroelectrode assembly which generally comprises an electrically nonconducting host membrane having a plurality of micro-sized pores extending through the membrane, and a macro-sized substrate electrode in contact with this host membrane. The host membrane has its pores impregnated with an electrically conductive medium, and the substrate electrode is in electrical contact with the impregnated pores of the host membrane. The electrically conductive medium is a carbon paste, and the substrate electrode includes a confined volume of such carbon paste in contact with an interior surface of the impregnated membrane.

5 Claims, 3 Drawing Sheets

ULTRAMICROELECTRODE ENSEMBLES

BACKGROUND AND SUMMARY OF THE INVENTION

The present invention relates generally to electrochemical electrode constructions, and particularly to ultramicroelectrode structures and methods of constructing such ultramicroelectrode structures.

An "ultramicroelectrode" may be defined as an electrode which has at least one dimension which is 10 μm or less. Thus, for example, an ultramicroelectrode may be a disk with a radius less than or equal to 10 μm, or a ring having its electrically conductive width less than or equal to this dimension. Alternatively, the ultramicroelectrode could be a band of undetermined length, which has a width less than or equal to 10 μm. In contrast, a "microelectrode" typically has its dimensions on the order of one to several millimeters.

Ultramicroelectrodes are useful for several reasons. Firstly, electrochemical experiments can be conducted in highly electrically resistive media. Secondly, chemical or electrochemical processes which are too fast for larger electrodes can be studied using an ultramicroelectrode. Additionally, the mass transport rate to an ultramicroelectrode is higher than that can be achieved using larger electrodes. Furthermore, lower detection limits can be achieved using an ultramicroelectrode, due to its higher signal-to-background ratio. Finally, steady-state signals, as opposed to transient signals can often be obtained with ultramicroelectrodes.

While ultramicroelectrodes provide enhanced analytical sensitivity in comparison with other electrode structures, one disadvantage of the ultramicroelectrode is that only very small currents can be obtained at such a minuscule electrode. However, this problem can be solved by constructing an ultramicroelectrode array or ensemble. In this regard, the term array is sometimes used to refer to assemblies where a plurality of ultramicroelectrodes are evenly spaced from each other, while the term ensemble is sometimes used to indicate that the ultramicroelectrode elements are not necessarily evenly spaced from each other. In any case, the total measured current from such ultramicroelectrode assemblies is the sum of the currents obtained at each of the ultramicroelectrode elements in the assembly.

One pertinent example of an ultramicroelectrode ensemble is discussed in "Preparation and Electrochemical Characterization of Ultramicroelectrode Ensembles", by Reginald M. Penner and Charles R. Martin, Anal. Chem. 1987, 59, 2625–2630. This article discloses a procedure for preparing ultramicrodisk electrode ensembles, and is hereby incorporated by reference. Specifically, this article discloses a method in which platinum is electrochemically deposited into the pores of a microporous polycarbonate host membrane until the platinum layer begins to overgrow the surface of the host membrane. The surface of this composite membrane is then impregnated with polyethylene by immersion, and the polyethylene and excess platinum are subsequently removed by polishing. This ultramicrodisk membrane is then stretched over a convex electrode, and held in place with a sleeve of heat shrinkable Teflon tubing. The host membrane used in this procedure is a Nuclepore ® polycarbonate membrane from Nuclepore, Inc.

It is a principal objective of the present invention to provide an ultramicroelectrode assembly and method of construction which does not require an electrochemical deposition step, nor requires the use of precious metals in the construction.

It is also a principal objective of the present invention to demonstrate that an ultramicroelectrode assembly can yield lower electroanalytical detection limits.

It is another objective of the present invention to provide a quick and inexpensive method of making an ultramicroelectrode assembly.

It is an additional objective of the present invention to provide an ultramicroelectrode assembly which is capable of demonstrating all three of the theoretically predicted electrochemical response limiting cases.

It is a further objective of the present invention to provide an ultramicroelectrode assembly which exhibits low capacitive currents.

To achieve the foregoing objectives, the present invention provides an ultramicroelectrode assembly which generally comprises an electrically nonconducting host membrane having a plurality of micro-sized pores extending through the membrane, and a macro-sized substrate electrode in contact with this host membrane. The host membrane has its pores impregnated with an electrically conductive medium, and the substrate electrode is in electrical contact with the impregnated pores of the host membrane. The electrically conductive medium is a carbon paste, and the substrate electrode includes a confined volume of such carbon paste in contact with an interior surface of the impregnated membrane.

The method of making an ultramicroelectrode assembly according to the present invention includes the steps of preparing the carbon paste, forcing the carbon paste into and through the pores of the host electrode, and joining the impregnated membrane to the substrate electrode. This assembly may also be heated in an oven to improve the adhesion between the impregnated membrane and the carbon paste substrate electrode.

Additional advantages and features of the present invention will become apparent from a reading of the detailed description of the preferred embodiments which makes reference to the following set of drawings in which:

DETAILED DESCRIPTION OF THE PREFERRED EMBODIMENT

Figure 1:
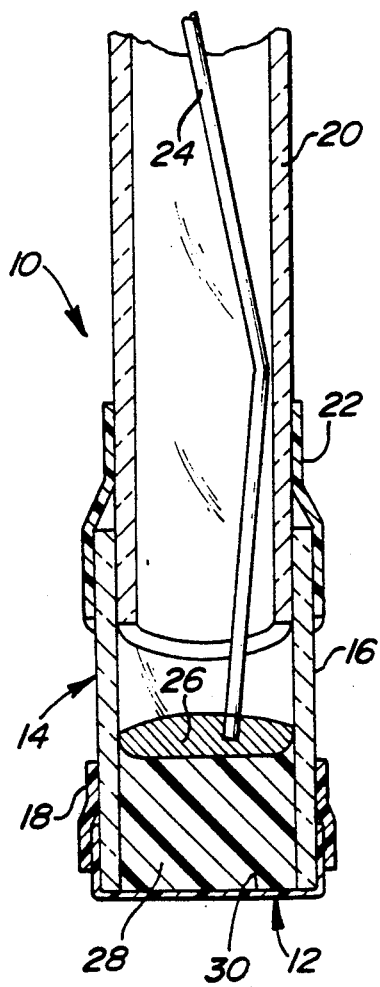
FIG. 1 is a cross-sectional view of an ultramicroelectrode assembly according to the present invention.

Referring to FIG. 1, an ultramicroelectrode assembly 10 according to the present invention is shown. The ultramicroelectrode assembly 10 is generally comprised of a host membrane 12 which is supported by a macro-sized substrate electrode 14. As will be more fully discussed below, the host membrane is impregnated with a carbon paste. The substrate electrode 14 is referred to as being "macro-sized" in that its dimensions are several orders of magnitude greater than the dimensions of the "micro-sized" pores of the host membrane 12. Thus, for example, the substrate electrode 14 includes a glass tube housing 16 which may have a radius measured in centimeters; whereas, the pores of the host membrane 12 will have a radius which is equal to or less than ten micrometers.

The host membrane 12 is stretched over one end of the tube 16 and held in place by annular member 18. In one embodiment according to the present invention, the annular member 18 is an elastomeric band or o-ring. The substrate electrode 14 may also include another glass tube 20 which is joined to the opposite end of tube 16 via heat shrinkable Teflon tube 22. However, it should be appreciated that the principals of the present invention are not dependent upon any particular housing construction for the substrate electrode 14.

A copper wire 24 is used to provide an electrical connection between the ultramicroelectrode assembly 10 and the conventional electrochemical instrumentation which employs the ultramicroelectrode assembly. Electrical contact between the copper wire 24 and the substrate electrode 14 may be provided by any suitable means, such as a drop 26 of mercury placed on top of the carbon paste 28. Electrical contact between the substrate electrode 14 and the host membrane is provided by placing a supply of carbon paste 28 in the end of the tube 16, such that this paste covers substantially the entire interior surface 30 of the host membrane 12.

Figure 2:
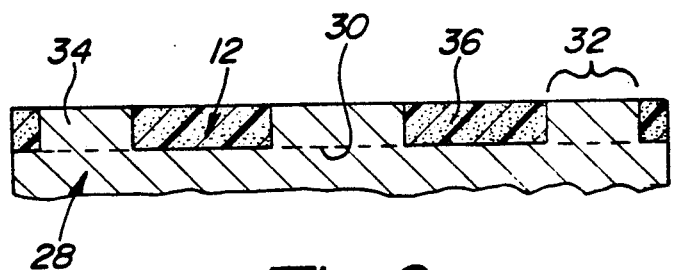
FIG. 2 is a magnified partial cross-sectional view of the interface between the host membrane and the substrate electrode shown in FIG. 1.

In this regard, FIG. 2 shows a greatly magnified cross-sectional view of a small portion of the interface between the host membrane 12 and the substrate electrode 14. As may be seen in FIG. 2, the host membrane 12 includes an array or ensemble of micro-sized pores 32 having a generally cylindrical shape. The pores 32 extend completely through the host membrane 12 and are filled with a carbon paste 34, such that each impregnated pore creates an ultramicroelectrode. The pores 32 are separated by the electrically nonconductive regions 36 of the host membrane 12, such that the active surface area of the ultramicroelectrode assembly 10 is only a fraction of the geometric surface area of the host membrane.

In one form of the present invention, it is preferred that the carbon paste 28 and the carbon paste 34 be substantially identical in composition. FIG. 2 also illustrates that the carbon paste ultramicroelectrodes 34 are in such substantial or intimate contact with the carbon paste 28 of the substrate electrode that there is essentially no boundary between them. Thus, the carbon paste 28 of the substrate electrode 14 will preferably be an extension of the ultramicroelectrodes 34, and this construction will provide a convenient way of collecting the currents obtained at each of the ultramicroelectrodes 34.

With respect to the material used for the host membrane 12, it is preferred that the host membrane 12 be a Nuclepore ® polycarbonate membrane, as these membranes provide linear, cylindrical pores of nearly uniform pore diameter. The specifications for one example of a suitable Nuclepore ® membrane are set forth in the Table below:

TABLE

| Pore[a] radius ($\mu$m) | Pore[a] density (pores cm$-2$) | Fractional[a,b] pore area | Thickness a ($\mu$m) | Ave. dis.[c] between pores ($\mu$m) |
| --- | --- | --- | --- | --- |
| 4.0 | 1 × 10[5] | 0.05 | 10 | 24 |

[a]From Nuclepore, Inc. product literature. Nominal precision of pore diameter is +0% to −20%. Nominal precision of pore density is −/− 15%.
[b]Surface area of pores divided by total surface of the membrane. Since the pores of the membrane become the ultramicroelectrode elements, this fraction is the electrochemically active area divided by the geometric area.
[c]Average distances are calculated from pore radii and densities, assuming regularly spaced pores.

While Nuclepore ® membranes are preferred, it should be understood that other suitable electrically nonconductive membrane materials may be used, providing they are inert to the chemistry of the application and have the pore structures necessary to create the ultramicroelectrode elements. Thus, for example other polymer materials may be used after they have been bombarded with fission fragments and chemically etched to enlarge the tracks created into micro-sized pores. Inorganic materials such as mica may also be used.

With respect to the method of making the ultramicroelectrode assembly 10 according to the present invention, the carbon paste was first prepared by intimately mixing carbon powder (Carbopack C, 80/100 mesh, Supelco, Belletonte, PA) with silicon-based high vacuum grease (Dow Corning) using a glass mortar and pestle. The Supelco carbon was selected for its small uniform size spherical particles and high electrical conductivity. In one example according to the present invention, 1.0 grams of the carbon powder was mixed with 1.0 grams of the vacuum grease. While in another example, 0.42 grams of the carbon powder was mixed with 0.20 grams of the vacuum grease. In general, the ratio of carbon power to vacuum grease should be such as to provide sufficient electrical conductivity, while still providing adequate binding of the carbon particles.

The Nuclepore ® membrane 12 was stripped of its wetting agent, polyvinylpyrrolidone, by sonicating in glacial acetic acid and followed by washing with purified water. The water was purified by passing distilled water through a Milli-Q water purification system. This stripping step was used to insure that that any aqueous solution did not leak into the interface between the host membrane 12 and the substrate electrode 14.

Nuclepore ® membranes generally have a smooth (shiny) face and a rough (dull) face. The carbon paste was applied to the dull face of the membrane 12, and the pestle was used to rub the paste into and through the pores 32 of the membrane. This procedure was continued until the carbon paste began to leak out from the opposite (shiny) side of the membrane 12. The carbon paste-impregnated membrane 12 was then applied to the surface of the carbon paste substrate electrode 14, with the dull surface of the membrane facing the carbon paste 28 of the substrate electrode. Excess carbon paste was removed from the exposed surface of the impregnated membrane 12 by polishing this surface on a sheet of glycine paper.

The assembly 10 was then heated in an oven at 100° C. for 20 minutes to improve the adhesion between the membrane 12 and the carbon paste substrate electrode 14. The surface of the impregnated membrane 12 was then polished once more while it was still warm. It should be noted that if any defects are observed in the seal between the interior surface 30 of the impregnated membrane 12 and the carbon paste substrate electrode 14, more carbon paste may be applied to the exposed surface of the membrane to fill in such defects. The membrane 12 may then be repolished.

In this regard, it should be noted that one of the advantages of this carbon paste construction is that it permits the active surface area of the ultramicroelectrode assembly to be renewable by polishing off old paste from the surface and forcing new paste into the pores 32 of the membrane 12. It should also be appreciated that this carbon paste construction is very inexpensive, and it permits the ultramicroelectrode assembly to be molded or formed into a variety of desirable shapes.

While carbon powder has been found to be quite effective, it may be possible to construct ultramicroelectrode assemblies according to the present invention using other electrically conductive, micro-sized particles. Thus, for example, it may be possible to use carbon black or furnace black. Similarly, it may be possible in the appropriate application to use other suitable electrically nonconducting materials as a binder, besides high vacuum grease. For example, polymeric materials such as polyethylene or polypropylene may serve as the binder. However, the binding material chosen must be capable of adhering to the surface of the membrane 12. Additionally, it should be appreciated that the use of highly viscous fluids, such as high vacuum grease, provide a particularly advantageous non-conductive material for suspending the carbon particles.

Figure 3A:
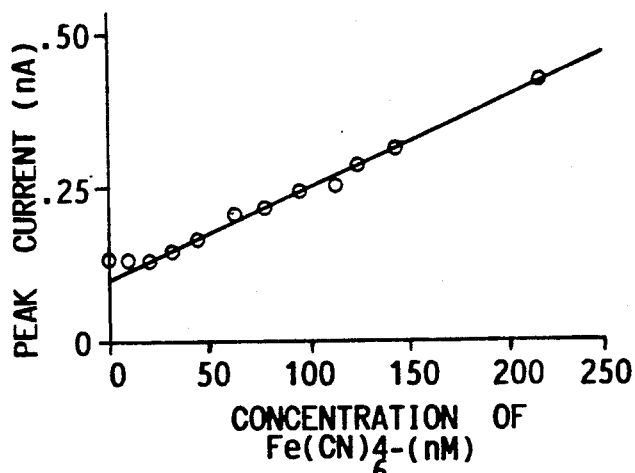
FIG. 3A is a graph of a calibration curve for the voltammetric determination of ferrocyanide using an ultramicroelectrode according to the present invention.
Figure 3B:
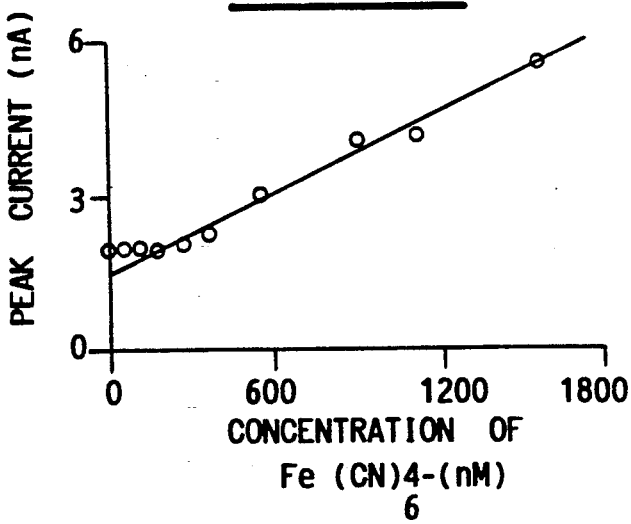
FIG. 3B is a graph of a calibration curve for the voltammetric determination of ferrocyanide using a macro-sized electrode.

Referring generally to FIGS. 3 and 4, the ability of the ultramicroelectrode assembly 10 to yield enhanced sensitivity in electroanalysis will now be discussed. First, with respect to the examples of FIG. 3A and FIG. 3B, the ultramicroelectrode assembly 10 and a carbon paste macro-sized electrode were alternatively placed into an analyte solution containing 0.5M $H_2SO_4$ and various concentrations of $Fe(CN)_6^{-4}$. A suitable reference electrode (e.g., a saturated calomel electrode) and a counter electrode (e.g., a Pt-Flag electrode) were also placed into the solution. Linear sweep voltammetry was used to effect the oxidation of this ion to $Fe(CN)_6^{3-}$ for various concentrations of this ferrocyanide analyte.

FIG. 3A illustrates a calibration curve of the peak current obtained as a function of the concentration of ferrocyanide, using 3.0 μm ultramicroelectrode elements. In this regard, it should be observed that this calibration curve is linear down to at least $10^{-7}$M. This detection limit is on the order of seven times lower than the detection limit obtained using the macro-sized electrode (0.071 cm2 electrode area), as shown in FIG. 3B.

Figure 4A:
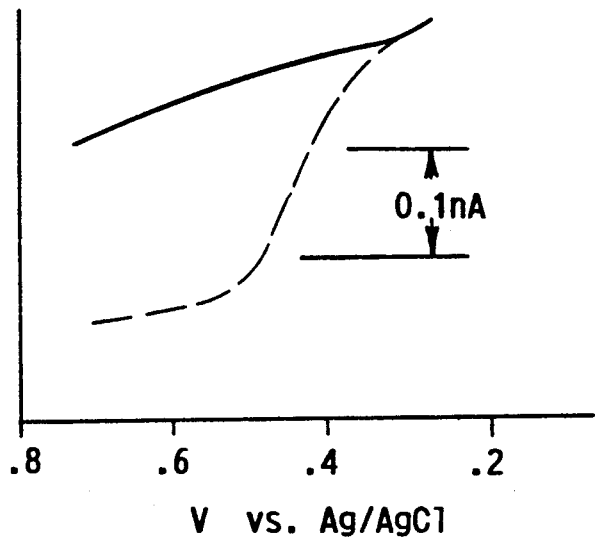
FIG. 4A is a graph comparing the faradaic current with the background current for the voltammetric determination of ferrocyanide using an ultramicroelectrode assembly according to the present invention.
Figure 4B:
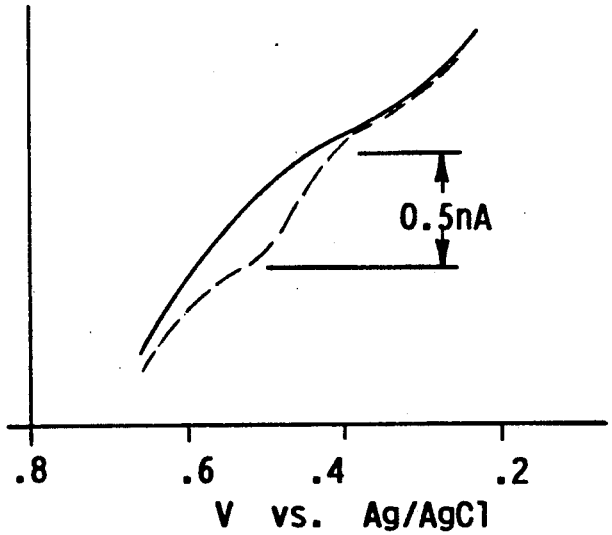
FIG. 4B is a graph comparing the faradaic current with the background current for the voltammetric determination of ferrocyanide using a macro-sized electrode.

The capacitive (background) current arises from double layer charging at the electrode surface. This background can limit the detection of electroactive species by masking the faradaic current. This is demonstrated in FIGS. 4A and 4B, where the solution is 0.12 μm ferrocyanide, and the faradaic signal results from the oxidation of ferrocyanide. As shown in FIG. 4B, the faradaic signal is barely perceptible over the background using the macro-sized electrode. However, with the ultramicroelectrode assembly 10, FIG. 4A shows that the faradaic signal is considerably more apparent over the background. By decreasing the active area of the electrode it is possible to decrease the capacitive current and allow the faradaic signal to remain the same. This is because capacitive currents are directly proportional only to the electrochemically active area of the electrode, whereas the faradaic signal is proportional to the total (active plus inactive) area of the electrode at slow scan rates (e.g., 5 mV/S).

Figure 5A:
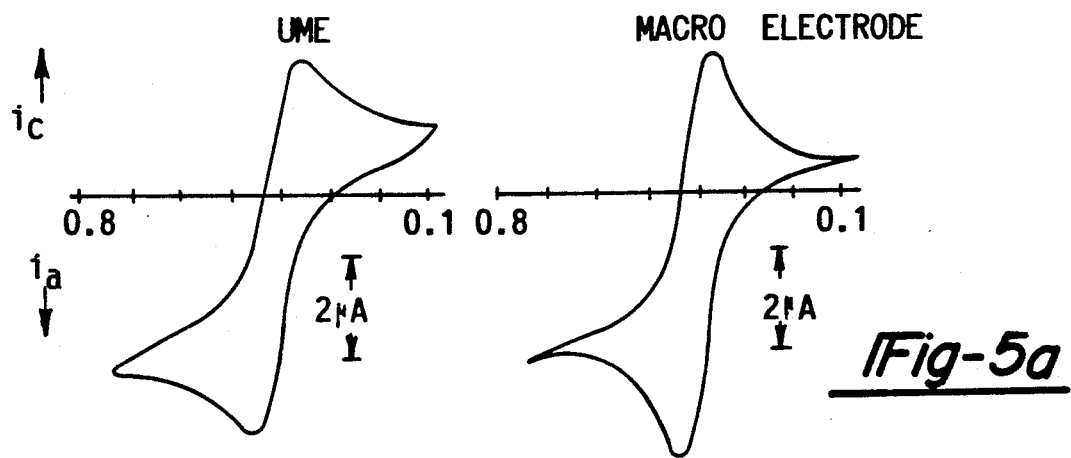
FIGS. 5A–5C are cyclic voltammograms which demonstrate that the ultramicroelectrode assembly according to the present invention is capable of verifying all three theoretical limiting cases.
Figure 5B:
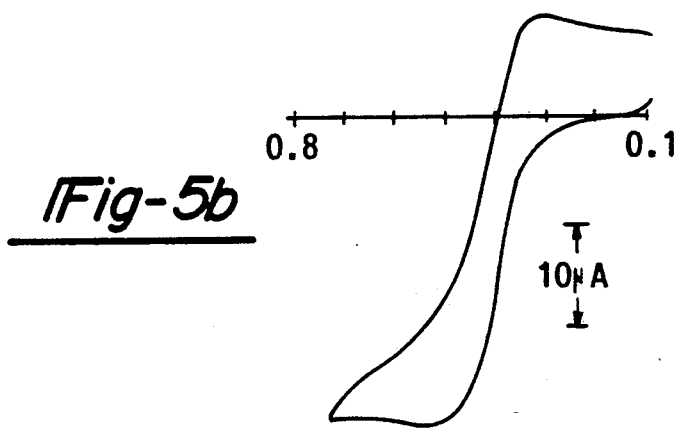
Figure 5C:
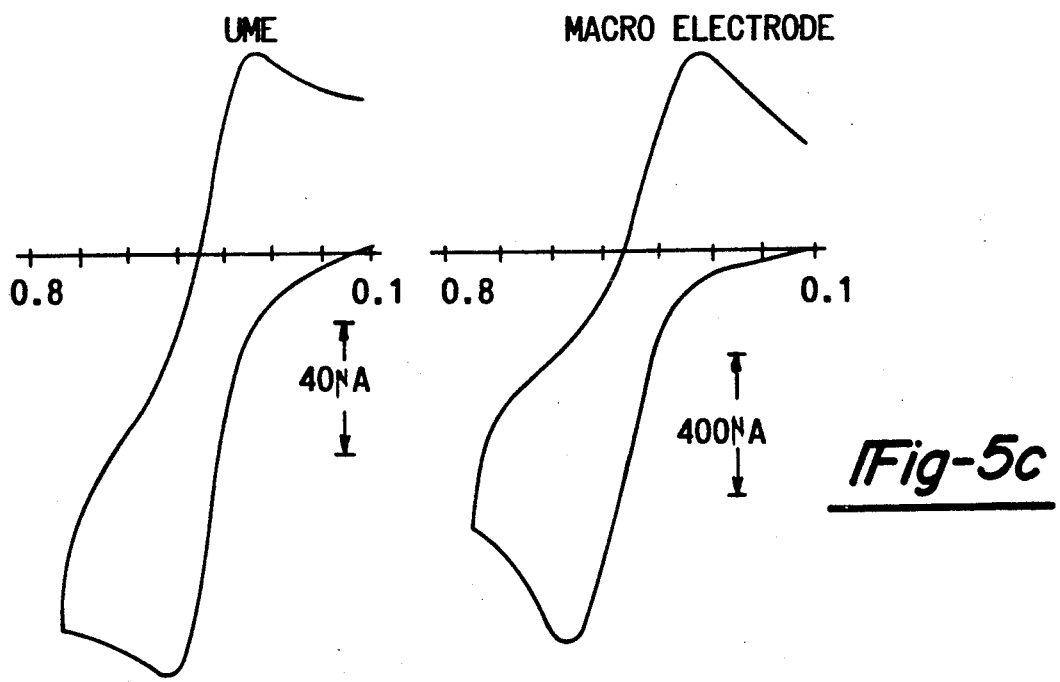

Referring now to FIG. 5A–5C, three cyclic voltammograms are shown to demonstrate that the ultramicroelectrode assembly 10 is capable of verifying all three theoretical limiting cases. In this regard, these cyclic voltammograms were obtained using a PARC model 175 programmer in conjunction with a PARC 173 potentiostat, and either a Soltec VP-64245 X-Y recorder or a Nicolet 206 digital oscilloscope. Again, a three electrode cell comprising a carbon paste working electrode (either assembly 10 or the macro-sized electrode), a Ag/AgCL reference electrode and a Pt-Flag counter electrode was used. 0.1M KCL served as the supporting electrolyte.

The shape of the cyclic voltammogram using an ultramicroelectrode assembly depends on the time scale (scan rate) of the experiment. The first limiting case is obtained at very high scan rates (e.g., greater than 100 V/s), where the diffusion layers at the ensemble elements are thin, linear and completely isolated. This linear diffusion situation produces a conventional, peak-shaped voltammogram, where currents are proportional to the electrochemically active surface area.

The second limiting case occurs at lower scan rates (e.g., 0.5 V/s), where the diffusion layers take on a radial character. This radial diffusion field yields sigmoidal voltammograms. The final limiting case occurs at very low scan rates (e.g., less than 10 mV/s) where the radial diffusion layers merge, yielding a net linear diffusion field. Because linear diffusion is obtained, a peak-shaped voltammogram is again observed. However, in this case, currents are proportional to the entire geometric area of the membrane for the ultramicroelectrode assembly.

In this regard, FIG. 5A shows slow scan voltammogram for ferrocenylmethyl trimethyl ammonium at the ultramicroelectrode assembly 10 and at the carbon paste macro-sized electrode of equivalent geometric area. A conventional, peak-shaped voltammogram is obtained at the assembly 10, and peak currents at the assembly 10 and macro-sized electrode are almost identical. This demonstrates that the assembly 10 can achieve the third limiting.

At the higher scan rates of FIG. 5B, the ferrocenylmethyl trimethyl ammonium voltammogram takes on a sigmoidal shape, indicating approach to the second limiting case. FIG. 5C shows voltammograms at very high scan rates. In agreement with the predictions of the third limiting case, the assembly 10 voltammogram again becomes peak-shaped and current is proportional to only the electrochemically active area.

It will be appreciated that the above disclosed embodiment is well calculated to achieve the aforementioned objects of the present invention. In addition, it is evident that those skilled in the art, once given the benefit of the foregoing disclosure, may now make modifications of the specific embodiment described herein without departing from the spirit of the present invention. Such modifications are to be considered within the scope of the present invention which is limited solely by the scope and spirit of the appended claims.

What is claimed is:

1. An ultramicroelectrode assembly, comprising:
   a tubular housing having two ends and a hollow interior, said hollow interior for confining an electrically conductive medium at one of said ends;
   an electronically conductive carbon paste disposed within and confined by said tubular housing;
   an electrical connector extending from said conductive carbon paste within said hollow tubular interior and adapted for connection to an instrument;
   an electrically non-conductive membrane operably associated with one end of said tubular housing to further help confine said electrically conductive carbon paste within said tubular housing;
   means for providing electrical contact between said electrical connector and said carbon paste, said electrical contact means being within said hollow interior and abutting said conductive carbon paste;
   said electrically non-conductive membrane having a plurality of micro-size pores, said electrically conductive carbon paste extending into said pores, said plurality of pores of said electrically non-conductive membrane defining a like plurality of ultramicroelectrodes and said carbon paste includes a supply of carbon particles suspended in a viscous fluid.

2. The ultramicroelectrode assembly according to claim 1, wherein said carbon particles are micro-sized.

3. The ultramicroelectrode assembly according to claim 2, wherein said viscous fluid is high vacuum grease.

4. The ultramicroelectrode assembly according to claim 1, wherein said membrane is a polymer which has been bombarded with fission fragments and chemically track-etched to form said micro-sized pores.

5. The ultramicroelectrode assembly according to claim 4, wherein said polymer membrane is a polycarbonate membrane.

* * * * *